US009927342B2

(12) United States Patent
Gaskill-Fox et al.

(10) Patent No.: US 9,927,342 B2
(45) Date of Patent: Mar. 27, 2018

(54) TWO STATION SAMPLE AND WASHING SYSTEM

(71) Applicant: Bio-Rad Laboratories, Inc., Hercules, CA (US)

(72) Inventors: Nathan Michael Gaskill-Fox, Fort Collins, CO (US); Daniel N. Fox, Bellvue, CO (US); Rodney C. Harris, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 777 days.

(21) Appl. No.: 13/923,148

(22) Filed: Jun. 20, 2013

(65) Prior Publication Data

US 2013/0340795 A1  Dec. 26, 2013

Related U.S. Application Data

(60) Provisional application No. 61/663,026, filed on Jun. 22, 2012.

(51) Int. Cl.
*G01N 35/10* (2006.01)
*G01N 11/02* (2006.01)
*G01N 15/14* (2006.01)

(52) U.S. Cl.
CPC .......... *G01N 11/02* (2013.01); *G01N 15/1404* (2013.01); *G01N 35/1004* (2013.01)

(58) Field of Classification Search
CPC ............... G01N 35/10; G01N 35/1004; G01N 35/1048; G01N 35/1051; G01N 35/1062;
(Continued)

(56) References Cited

U.S. PATENT DOCUMENTS 3,269,800 A * 8/1966 Lukrec ................... G01N 35/10
141/243
3,443,439 A * 5/1969 Cruz ..................... G01N 35/026
73/863.32
(Continued)

FOREIGN PATENT DOCUMENTS

CN 101135694 3/2008
CN 101363872 2/2009
(Continued)

OTHER PUBLICATIONS

International Preliminary Report on Patentability—PCT/US13/46872-ISA/US—Dec. 31, 2014.
(Continued)

*Primary Examiner* — Joseph L Perrin
*Assistant Examiner* — Irina Graf
(74) *Attorney, Agent, or Firm* — Weaver Austin Villeneuve & Sampson LLP

(57) ABSTRACT

Disclosed is a two station system for a flow cytometer that includes a sample station and a wash station. During washing, the user has access to the sample station to insert a new sample. This increases the efficiency of the workflow process. Rotary clamps are used to automatically clamp the sample station and wash station to the system. A low volume pressurized cavity is used to bring the pressure of the sample to a desired pressure, which further increases productivity of the system. A transparent body is provided in the sample station so a user can view the sample during the sampling process. A backwash process is used to clean the sample injection tube and the sample uptake tube. In addition, the wash station is designed to rinse the outer surface of the sample uptake tube.

12 Claims, 10 Drawing Sheets

(58) Field of Classification Search
CPC ........... G01N 35/1081; G01N 35/1083; G01N 11/12; G01N 15/1404
See application file for complete search history.

(56) References Cited

U.S. PATENT DOCUMENTS

| | | | | |
|---|---|---|---|---|
| 4,478,094 | A * | 10/1984 | Salomaa | G01N 1/38 422/552 |
| 4,554,839 | A * | 11/1985 | Hewett | B01L 3/5085 422/561 |
| 4,681,742 | A * | 7/1987 | Johnson | B01L 3/5085 356/246 |
| 4,873,875 | A * | 10/1989 | Cork | G01N 15/042 250/577 |
| 4,887,472 | A * | 12/1989 | Jansen | G01N 1/2035 73/863.86 |
| 5,147,551 | A * | 9/1992 | Averette | B01D 11/0219 210/472 |
| 5,182,617 | A | 1/1993 | Yoneyama et al. | |
| 5,380,487 | A | 1/1995 | Choperena et al. | |
| 5,395,588 | A | 3/1995 | North, Jr. et al. | |
| 5,580,524 | A | 12/1996 | Forrest et al. | |
| 5,882,597 | A * | 3/1999 | Astle | B01L 99/00 134/170 |
| 6,027,691 | A | 2/2000 | Watts et al. | |
| 6,133,045 | A * | 10/2000 | Johnson | B01L 3/50255 210/406 |
| 6,274,087 | B1 | 8/2001 | Preston et al. | |
| 6,562,299 | B1 * | 5/2003 | Ostgaard | B01L 3/50825 118/419 |
| 6,878,556 | B2 | 4/2005 | Sklar et al. | |
| 6,899,848 | B1 * | 5/2005 | Chen | G01N 35/028 422/535 |
| 7,220,385 | B2 | 5/2007 | Blecka et al. | |
| 7,452,510 | B2 | 11/2008 | Weinfield et al. | |
| 2001/0021354 | A1 * | 9/2001 | Lang | G01N 31/16 422/63 |
| 2001/0031223 | A1 * | 10/2001 | Lang | G01N 35/025 422/64 |
| 2002/0085959 | A1 * | 7/2002 | Carey | B01L 3/508 422/400 |
| 2002/0192113 | A1 | 12/2002 | Uffenheimer et al. | |
| 2003/0223472 | A1 | 12/2003 | Ravalico et al. | |
| 2005/0249635 | A1 | 11/2005 | Okun et al. | |
| 2007/0212784 | A1 | 9/2007 | Okun | |
| 2008/0098828 | A1 | 5/2008 | Li et al. | |
| 2008/0173577 | A1 * | 7/2008 | Roenneburg | B01D 15/247 210/198.2 |
| 2008/0219886 | A1 * | 9/2008 | Fukuju | B01L 9/06 422/63 |
| 2009/0035866 | A1 | 2/2009 | Wilson | |
| 2009/0041622 | A1 | 2/2009 | Maeda et al. | |
| 2009/0293644 | A1 | 12/2009 | Sancho | |
| 2009/0293910 | A1 | 12/2009 | Ball et al. | |
| 2011/0158848 | A1 | 6/2011 | Arima et al. | |
| 2012/0199612 | A1 * | 8/2012 | Demarest | B65D 83/207 222/394 |
| 2013/0233438 | A1 * | 9/2013 | Jimroglou | B67D 3/0061 141/11 |

FOREIGN PATENT DOCUMENTS

| | | |
|---|---|---|
| CN | 101529243 | 9/2009 |
| CN | 101634658 | 1/2010 |
| JP | 03-213528 | 9/1991 |
| JP | 2001-089425 | 4/2001 |
| JP | 2008-202945 | 9/2008 |
| WO | 2013/192442 | 12/2013 |

OTHER PUBLICATIONS

International Search Report and Written Opinion—PCT/US13/46872-ISA/US—Nov. 22, 2013.
Extended European Search Report—EP 13806788—Jun. 1, 2016.
Partial European Search Report—EP 13806788—Jan. 18, 2016.
Chinese First Office Action dated Jan. 5, 2016 issued in CN 201380032841.4.
Supplementary Extended European Search Report dated May 25, 2016 in EP Application No. 13806788.
Chinese Second Office Action dated Sep. 19, 2016 issued in CN 2013880032841.4.
Chinese Third Office Action dated Feb. 14, 2017 issued in CN 2013880032841.4.

* cited by examiner

TWO STATION SAMPLE AND WASHING SYSTEM

CROSS-REFERENCE TO RELATED APPLICATIONS

This application is based upon and claims priority to U.S. provisional application Ser. No. 61/663,026, filed Jun. 22, 2012, entitled "Two Station Sample and Washing Station," which application is specifically incorporated herein by reference for all that it discloses and teaches.

This application is related to U.S. Provisional Patent Application Ser. No. 61/656,934, filed Jun. 7, 2012, by Daniel N. Fox, Susan Hunter, Nathan Michael Gaskill-Fox, Kevin P. Raley and Richard A. Miles, entitled "Automated and Accurate Drop Delay for Flow Cytometry," U.S. Provisional Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," U.S. Provisional Patent Application filed on the same date as the present application, by Nathan M. Gaskill-Fox, Daniel N. Fox and Rodney C. Harris, entitled "Multi-Directional Sorting with Reduced Contamination in a Flow Cytometer," U.S. Provisional Patent Application filed on the same date of the present application, by Daniel N. Fox, Matthias J. G. Ottenberg and Kevin P. Raley, entitled "Condensed Geometry Nozzle for Flow Cytometry," and U.S. Provisional Patent Application filed on the same date as the present application, by Daniel N. Fox and Nathan M. Gaskill-Fox, entitled "Fluid Mixing and Rinsing System for a Flow Cytometer." All of these applications are hereby specifically incorporated herein by reference, for all that they disclose and teach.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest, which are collectively referred to herein as "particles." Sorting and analysis of these particles can provide valuable information to both researchers and clinicians. In addition, sorted particles can be used for various purposes to achieve a wide variety of desired results.

SUMMARY

An embodiment of the present invention may therefore comprise a two station sampling and washing system for a flow cytometer comprising: a wash station that washes parts of the flow cytometer that contact sample particles during a wash cycle; a sample station that provides access of the flow cytometer to samples during a sample cycle and is accessible to a user during the wash cycle so that the user can place samples in the sample station during the wash cycle; a clamp that automatically secures the wash station during the wash cycle and the sample station during the sample cycle.

An embodiment of the present invention may further comprise a process of sampling and washing using a two station system in a flow cytometer comprising: providing a wash station for washing parts during a wash cycle that contact sample particles in the flow cytometer; providing a sample station that supplies the sample particles to the flow cytometer during a sample cycle and is accessible to a user during the wash cycle so that the user can place samples in the sample station during the wash cycles; washing the parts during the wash cycle by causing a rinsing fluid to flow backwards through the parts and by injecting a rinse fluid around a sample pickup tube in the wash station.

DETAILED DESCRIPTION OF THE EMBODIMENTS

Figure 1:
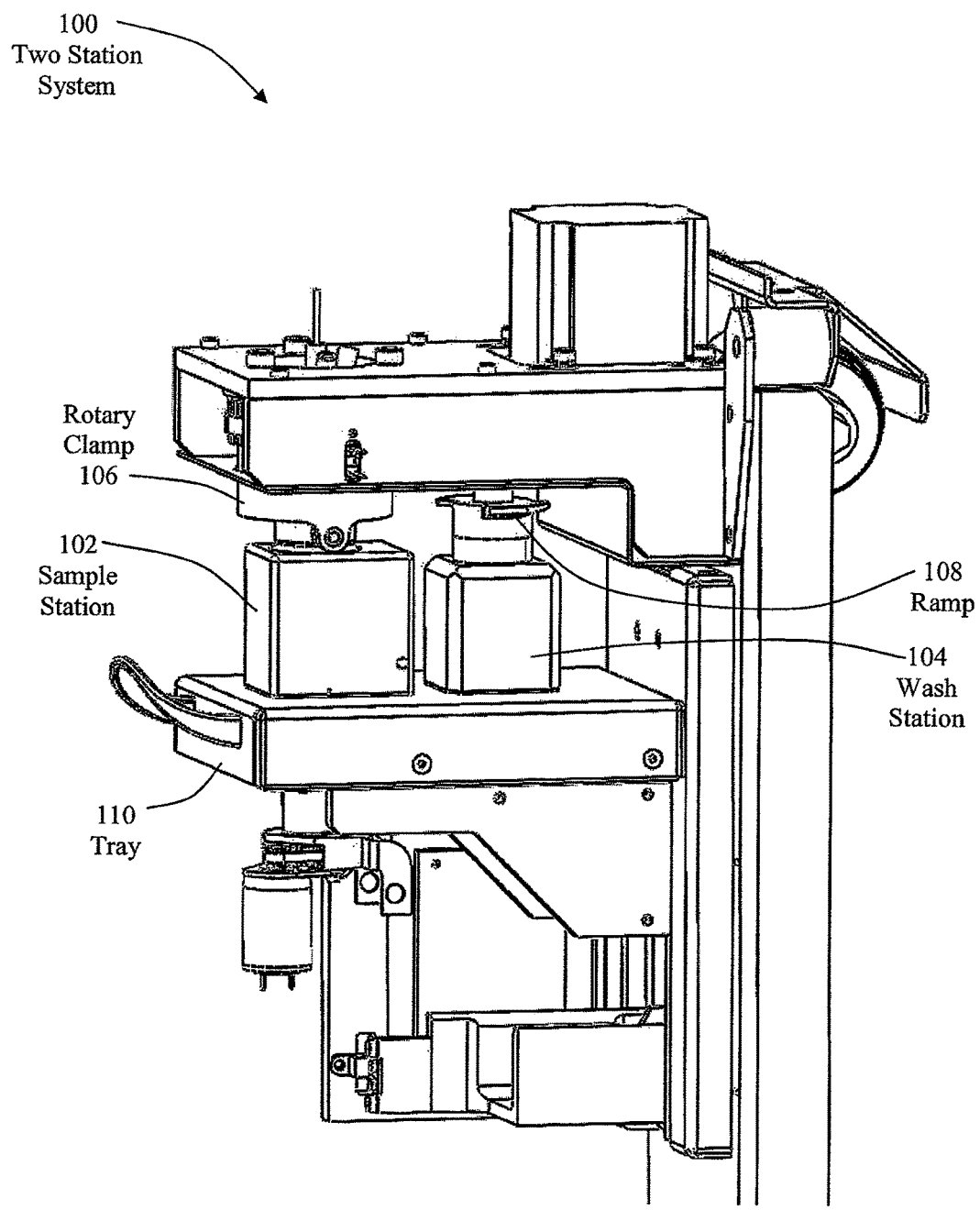
FIG. 1 is a schematic isometric view of an embodiment of a two station system in a sample cycle position.

FIG. 1 is an isometric view of an embodiment of a two station system 100 of a flow cytometer. The two station system 100 is illustrated in the sample position, with the clamp 106 shown as clamped to the sample station 102. The wash station 104 is in an idle position, as illustrated in FIG. 1. Both the sample station 102 and wash station 104 are disposed and attached to a tray 110 that moves the sample station 102 and wash station 104 into positions for clamping by the rotating clamp 106. While the two station system 100 is clamped by the rotating clamp 106 to the sample station, sample fluid is drawn from a sample container disposed in sample station 102 for sorting by a flow cytometer.

Figure 2:
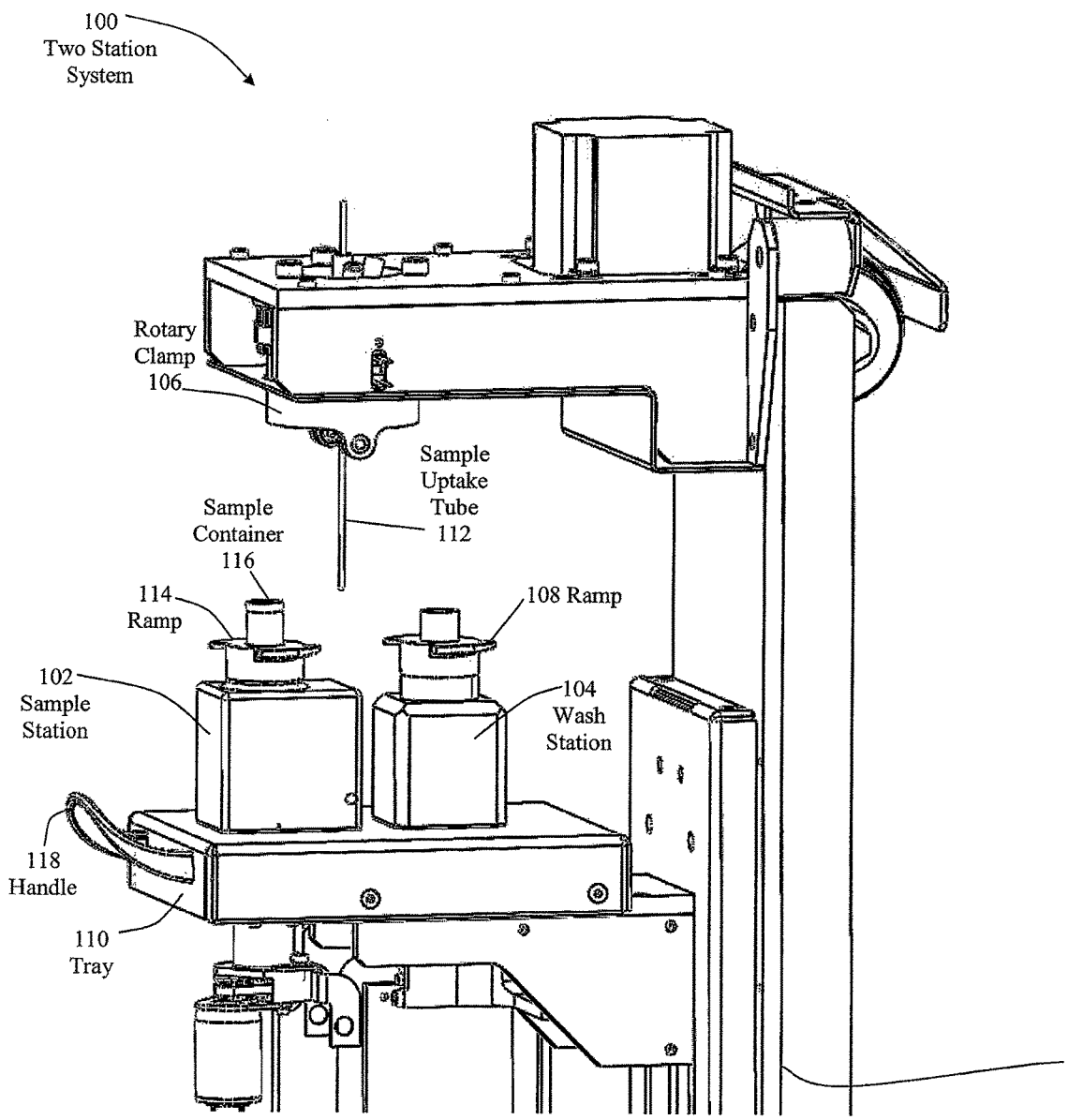
FIG. 2 is an isometric view of the embodiment of FIG. 1 in an intermediate position.

FIG. 2 is an isometric view of the embodiment of FIG. 1 illustrated in an intermediate position between the two stations of the two station system 100. As illustrated in FIG. 2, the tray 110 has been lowered to expose the sample uptake tube 112. The sample uptake tube 112 is the tube that draws the sample fluid from the sample container 116 for insertion into a nozzle of a flow cytometer. Rotating clamp 106 rotates to an open position and releases the ramp 114 of the sample station 102. The tray 110 can then be manually lowered using handle 118 and pulled laterally to the position shown in FIG. 2.

The tray 110, illustrated in FIG. 2, can be moved to the intermediate position when the sample in the sample container 116 is depleted, or if the process of sorting the sample cells in a flow cytometer has ceased for any reason. Once the sample uptake tube 112 has been removed from the sample container 116 in the sample station 102, sample cells remain in the sample uptake tube 112, as well as other portions of the system, such as the injection needle 158 (FIG. 7), sample tubing 160 (FIG. 7) and nozzle 156 (FIG. 7), to some extent. Assuming that a different sample is to be sorted in the flow cytometer, it is desirable to clean the sample uptake tube 112 and backwash the system 152 (FIG. 7) using the wash station 104. Wash station 104 has a ramp 108 that is similar to ramp 114, which engages the rotary clamp 106, as disclosed in more detail below.

Figure 3:
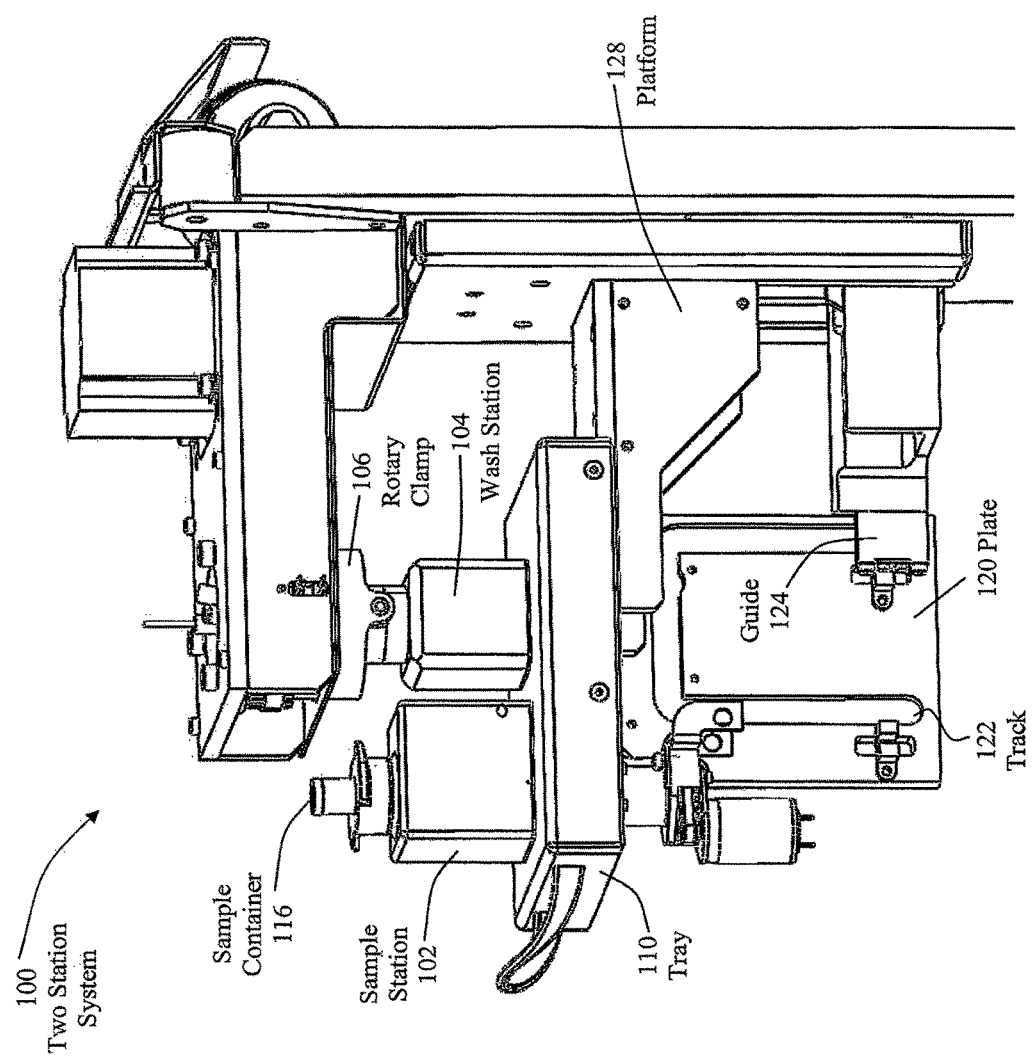
FIG. 3 is an isometric view of the embodiment of FIG. 1 in a cleaning cycle position.

FIG. 3 is an isometric view of the embodiment of FIGS. 1 and 2 shown in the cleaning position with rotary clamp 106 clamped to wash station 104. As illustrated in FIG. 3, the rotary clamp 106 has engaged the wash station 104 to perform a wash cycle. The tray 110 is moved to a position that is aligned with the rotary clamp 106, and the tray 110 is moved vertically to allow the rotary clamp 106 to engage wash station 104. The ramp 108 (FIG. 2) is engaged by the rotary clamp 106 and clamps the wash station 104 to the system. In this position, a backwash and a flushing procedure are performed, and the sample uptake tube 112 is cleaned on both interior and exterior surfaces, as set forth in more detail with respect to FIG. 7. The movement of the sample station 102 and wash station 104 on tray 110 is limited by the movement of the guide 124 in track 122 that is disposed on plate 120. The guide 124 is shown in the locked position on the track 122 when the wash station 104 is positioned and locked by the rotary clamp 106. By constraining the movement of tray 110 in the track 122, as illustrated in FIG. 3, precise movement and alignment of the two stations, i.e. the sample station 102 and the wash station 104, is achieved. Platform 128 provides a surface for lateral movement on bearing rollers (not shown) between the tray 110 and the platform 128.

As also shown in FIG. 3, the sample container 116 can be accessed by a user for removal and placement of a new sample container 116 in a sample station 102 during the wash cycle. This can occur while the wash station 104 is performing the process of washing the various parts including the sample uptake tube 112 that have contacted the sample, to ensure removal of sample particles. This prevents contamination of the new sample in a new sample container 116 placed in sample station 102 by a user.

Accordingly, the two station system illustrated in FIGS. 1, 2 and 3 allows a user to remove the sample container 116 while the two station system 100 is proceeding with the wash cycle. Users may have sample containers, such as sample container 116, stored in a cool location, such as a bucket of ice and simply remove the sample container 116 and replace the sample container with a new sample to be sorted while the wash cycle is being performed. In the embodiments of FIGS. 1, 2 and 3, the washing process performed by the wash station 104 includes backflow washing of the various parts that have been contact with the sample, as well as flushing of outside surfaces of an uptake sample tube, as explained in more detail with respect to FIG. 7. In one embodiment, the wash cycle process may take approximately 8 seconds. During that time, the sample container 116 can be replaced with a new sample, which speeds the overall work flow of the system. The two station configuration provides efficiency in the workflow process since the user can replace sample containers 116 while the various parts of the system are being cleaned. In addition, the rotary clamp 106 automatically locks when the wash station 104 is aligned with the rotary clamp 106 and automatically unlocks after the washing process has been completed. Similarly, when the sample station 102 is moved by the user to a position under the rotary clamp 106, the rotary clamp 106 is automatically actuated to rotate and seal to the sample station 102.

To simplify the two station system 100, illustrated in FIGS. 1-3, the sample container 116 is a standard size test tube container that has a volume of 5 mL. If additional sample is to be sorted, the sample can be divided between two or more sample containers 116. For example, if a 15 mL sample is to be sorted, three sample containers 116 can be utilized. Because the two station process provides an efficient workflow process, dividing larger samples between multiple containers does not significantly affect the overall time required to sort larger samples. The benefits of utilizing a single size sample container 116 outweigh any delay especially since the two station system 100 provides a very efficient workflow process. Frequent cleaning of the system is also beneficial. Workflow can also be improved by skipping the wash cycle during re-introduction of identical samples, which can be detected by the user returning the sample station 102 to the clamp 106 without first moving the wash station 104 to the clamp 106.

Figure 4:
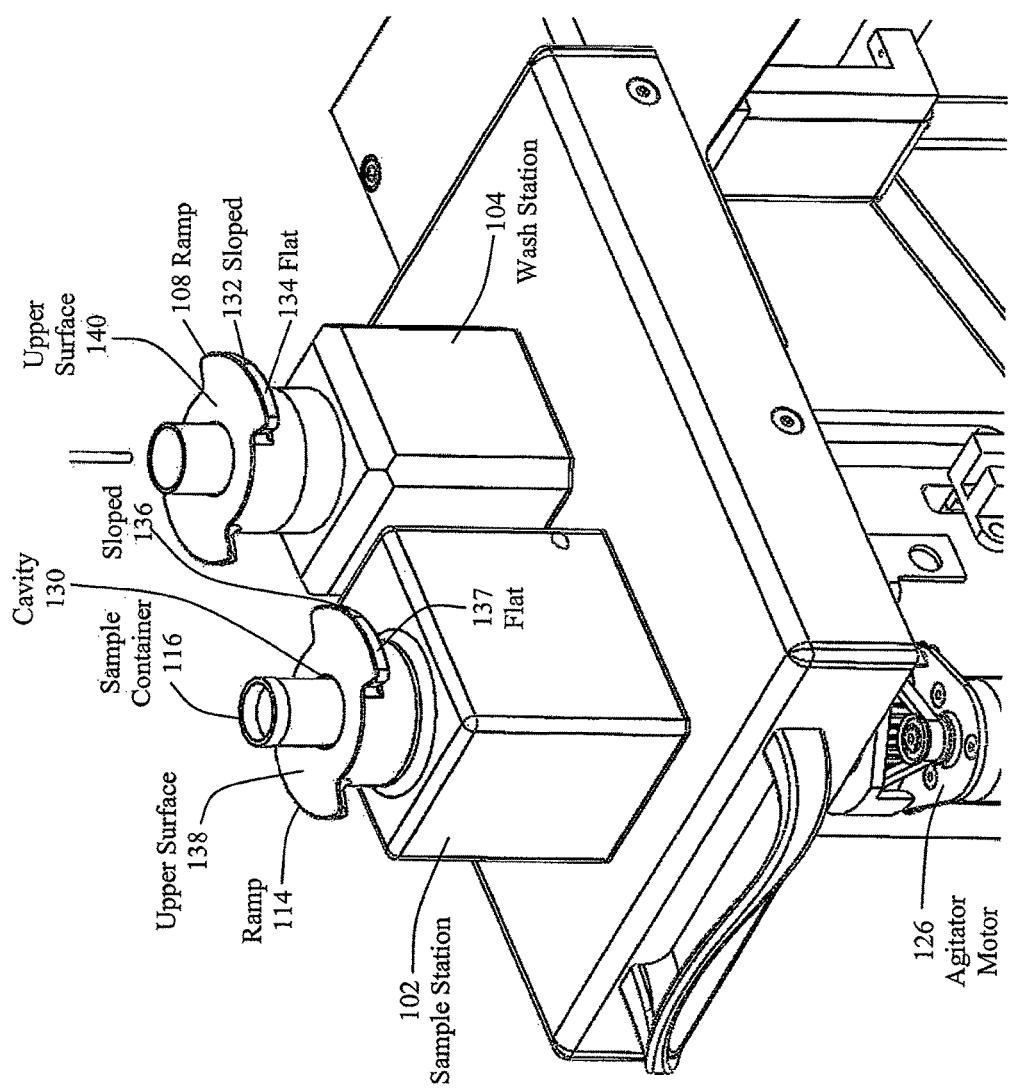
FIG. 4 is a close-up isometric view of the sample station and the cleaning station of the embodiment of FIG. 1.

FIG. 4 is an isometric view of the sample station 102 and the wash station 104. As shown in FIG. 4, the ramp 114 provides a locking mechanism for locking the sample station 102 using the rotary clamp 106. Ramp 114 has a sloped portion 136 and flat portion 137. The sample station 102 is sealed to the rotary clamp 106 on the upper surface 138 of the ramp 114. Similarly, ramp 108 has a sloped surface 132 and a flat surface 134. The wash station 104 is clamped to the rotary clamp 106 on the upper surface 140 of the ramp 108. An agitation motor 126 is also illustrated in FIG. 4 that provides agitation of sample container 116. The sample container 116 fits within the cavity 130 and is agitated by the agitation motor 126, as disclosed in more detail with respect to FIGS. 8 and 9.

Figure 5:
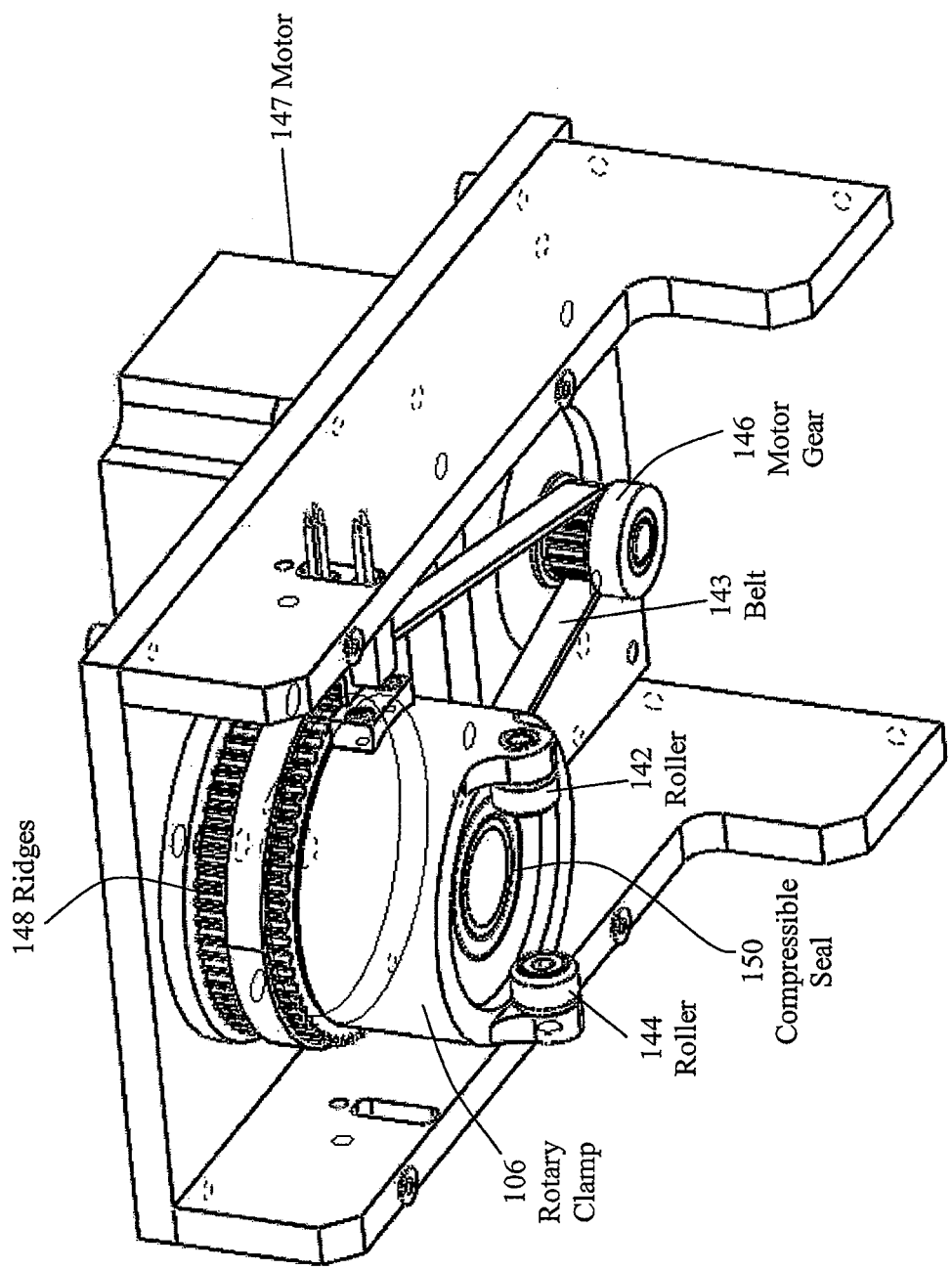
FIG. 5 is an isometric bottom view of an embodiment of a clamp.

FIG. 5 is an isometric bottom view of the clamp 106. As illustrated in FIG. 5, the rotary clamp 106 includes two rollers 142, 144. The compressible seal 150 seals the ramp 114 of the sample station 102 to the rotary clamp 106 and the ramp 108 of the wash station 104 to the rotary clamp 106. Compressible seal 150, which may comprise an o-ring that seals against the flat upper surface 138 of ramp 114 and the flat upper surface 140 of ramp 108. The assembly holding compressible seal 150 may also be spring loaded (not shown) to allow greater tolerance variability in the mating features of rollers 142 and 144 with ramps 114, 108 and flats 137, 134. The spring can be chosen such that the mating force is greater than the force generated by pressure inside the sample station 102 or wash station 104. Motor gear 146 drives belt 143, which in turn engages the ridges 148 to turn the rotary clamp 106. Motor gear 146 is coupled to a motor 147 that may comprise a servo or step motor that is programmed to automatically turn the rotary clamp 106 by the proper amount so that the rollers 142, 144 engage the ramps 114, 108. Similarly, the motor gear 146 rotates to move the belt 143 to engage and disengage the rollers 142, 144 from the ramps 114, 108.

Figure 6:
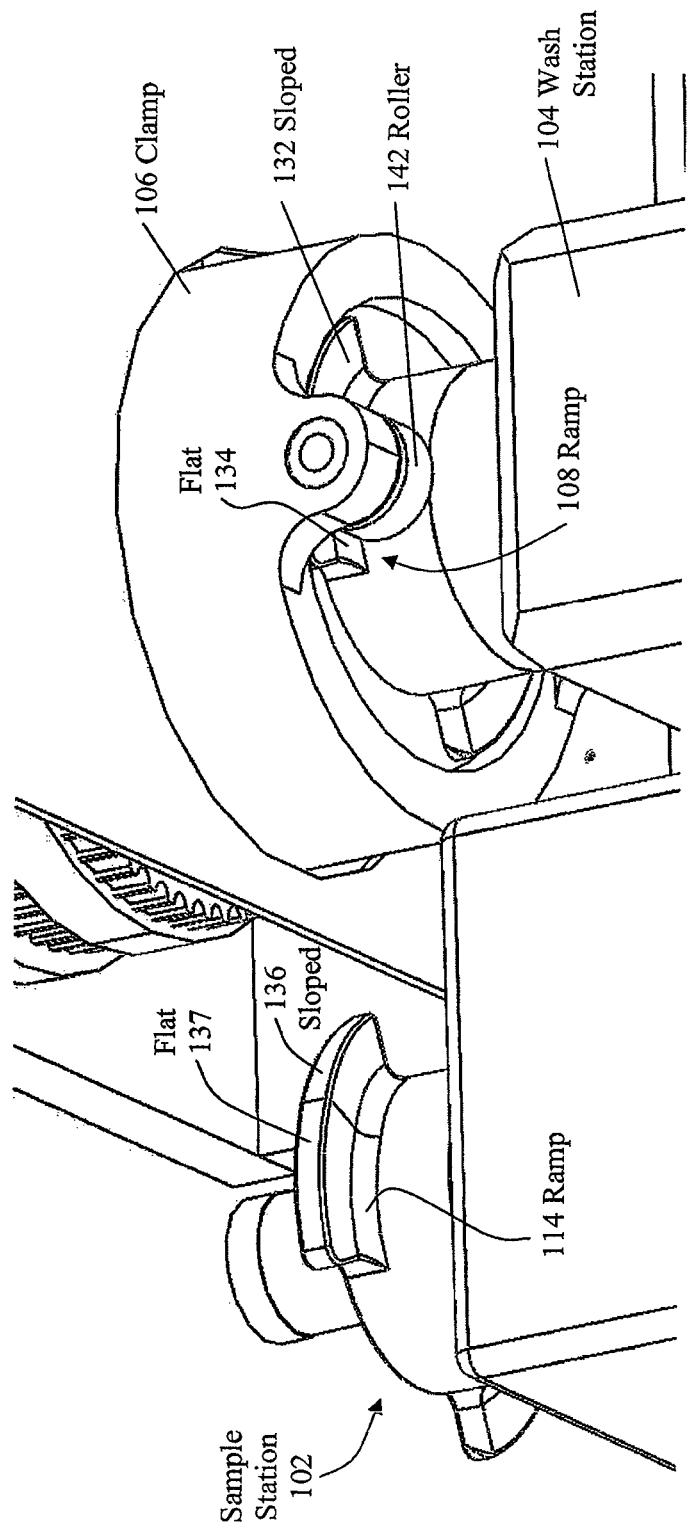
FIG. 6 is an isometric view of the clamp of FIG. 5 in a clamped position on a wash station.

FIG. 6 is an isometric close up view of the ramps 114, 108 and the clamp 106. As illustrated in FIG. 6, roller 142 of clamp 106 has engaged the flat portion 134 of the ramp 108 of the wash station 104. During the clamping process, roller 142 engages the sloped portion 132 and gradually causes the ramp 108 to be drawn upwardly to the clamp 106. Roller 142 then stops on the flat portion 134 of the ramp 108. The upward pressure generated by the roller 142 on the ramp 108 causes the upper surface 140 of ramp 108 to compress and seal against compressible seal 150. The height of the flat portion 134 creates a sufficient amount of pressure on the upper surface 140 of the ramp 108 to adequately seal the ramp 108 and the wash station 104 to the clamp 106 using compressible seal 150. In this embodiment, an o-ring is used as compressible seal 150 and is self-energized by the pressure of the air within pressurized cavity 174, allowing the compressible seal 150 to function over a wide range of pressures regardless of the actual clamping force generated by the clamp engagement. Similarly, clamp 106 engages the sloped portion 136 and flat portion 137 of the ramp 114 of the sample station 102. Roller 142 and roller 144 cause sufficient pressure on the ramp 114 to cause the upper surface 138 of ramp 114 to seal against the compressible seal 150, which seals the sample station 102 to the clamp 106.

Figure 7:
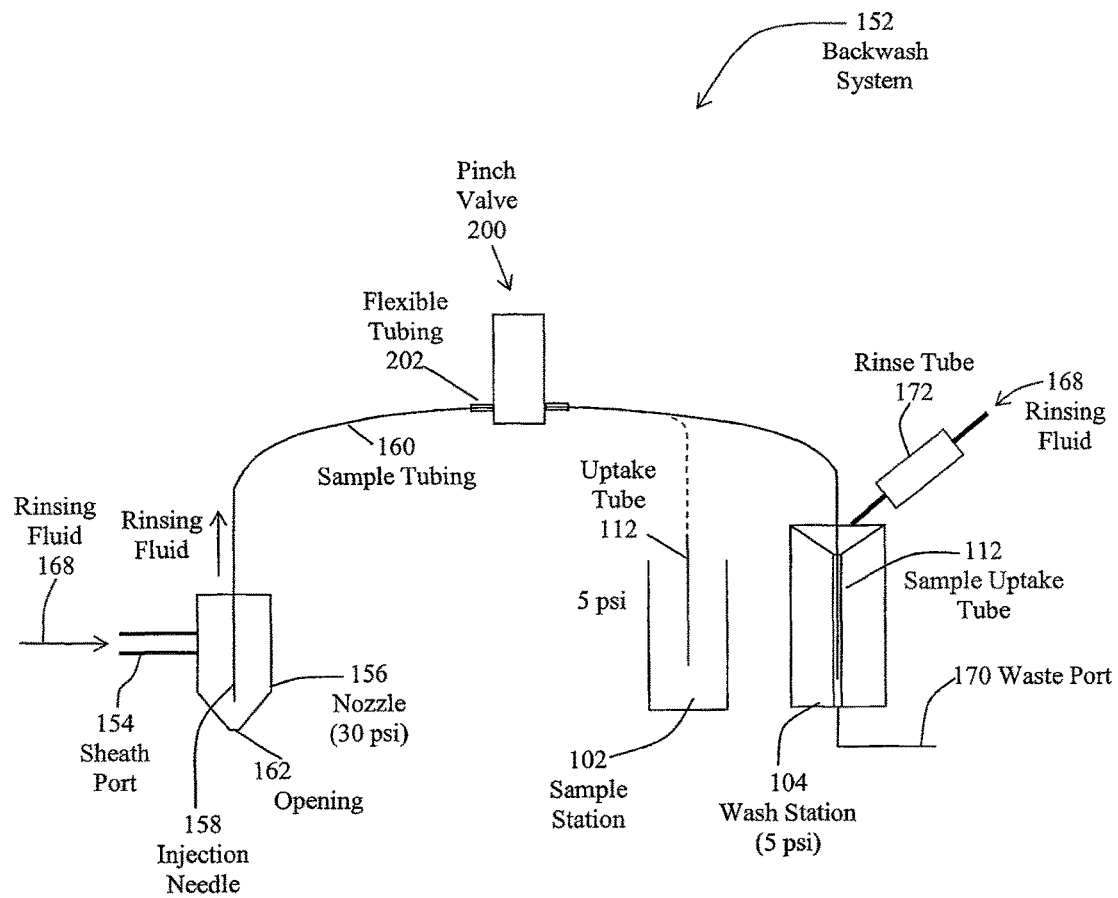
FIG. 7 is a schematic illustration of an embodiment of a backwash system.

FIG. 7 is a schematic diagram of a backwash and flushing system 152. As illustrated in FIG. 7, rinsing fluid enters a sheath port 154 during normal operation of the sample cycle of the flow cytometer, and prior to operation of the backwash and flushing system 152. The sheath port 154 supplies sheath fluid to the nozzle 156 at a pressure of approximately 30 psi, in one embodiment. During a normal sample cycle, sheath fluid flows through the bottom opening 162 of the nozzle 156. At the same time, sample fluid flows through the injection needle 158 at a slightly higher pressure than the sheath fluid to cause the sheath fluid and sample fluid to flow through the opening 162 at the bottom of the nozzle 156. During the sample process, the sample uptake tube 112 is located in the sample station 102. During the backwash phase, illustrated in FIG. 7, the sample uptake tube 112 is located in the wash station 104. The pressure in the wash station 104 is approximately 5 psi in one embodiment. Rinsing fluid then replaces the sheath fluid during the wash cycle. The rinsing fluid may comprise deionized water, or may simply comprise the sheath fluid. The rinsing fluid 168 is applied to the nozzle during the wash cycle 152, illustrated in FIG. 7, in the same manner as the sheath fluid is applied to the nozzle through sheath port 154, during the sample cycle. Accordingly, the pressure of the rinsing fluid in the nozzle 156 is approximately 30 psi. Rinsing fluid 168 flows into the nozzle 156, out of the nozzle opening 162, backwards through injection needle 158, backwards through the sample tubing 160, and backwards through the sample uptake tube 112, into the wash station 104. The backflow rinsing fluid 168 that is deposited in the wash station 104 is then evacuated to a waste port 170.

As also illustrated in FIG. 7, the rinse tube 172 injects rinsing fluid 168 into the wash station 104 at an angle so that the rinsing fluid 168 swirls around the outside of the sample uptake tube 112 and cleans the outside of the sample uptake tube 112. The swirling rinsing fluid 168 that is injected by the rinse tube 172 is then exhausted out of the waste port 170.

Hence, both the outside surface of the sample uptake tube 112, as well as the inside surface of the sample uptake tube 112, are washed with rinsing fluid 168. Also, the injection needle 158 and sample tubing 160 are also back flushed to the wash station 104. The sample uptake tube 112 is made from fluorinated ethylene propylene (FEP), and portions, such as the injection needle 158, are made from polyether ether ketone (PEEK) materials that are extremely smooth and resistant to collection of sample particles on the surface of the tube. As such, the backwash process, illustrated in FIG. 7, effectively removes sample particles from the system. At the same time, the sample station 166 is accessible to a user so that a new sample container 116 can be placed in the sample station 102.

As also illustrated in FIG. 7, a pinch valve 200 and length of flexible tubing 202 are utilized to allow sealing the sample tubing 160 during movement of the tray 110, or any time that sample introduction is not required and backflow washing is not required. The flexible tubing 202 is PharMed BPT and is also extremely smooth and resistant to collection of sample particles on the surface of the tube.

Figure 8:
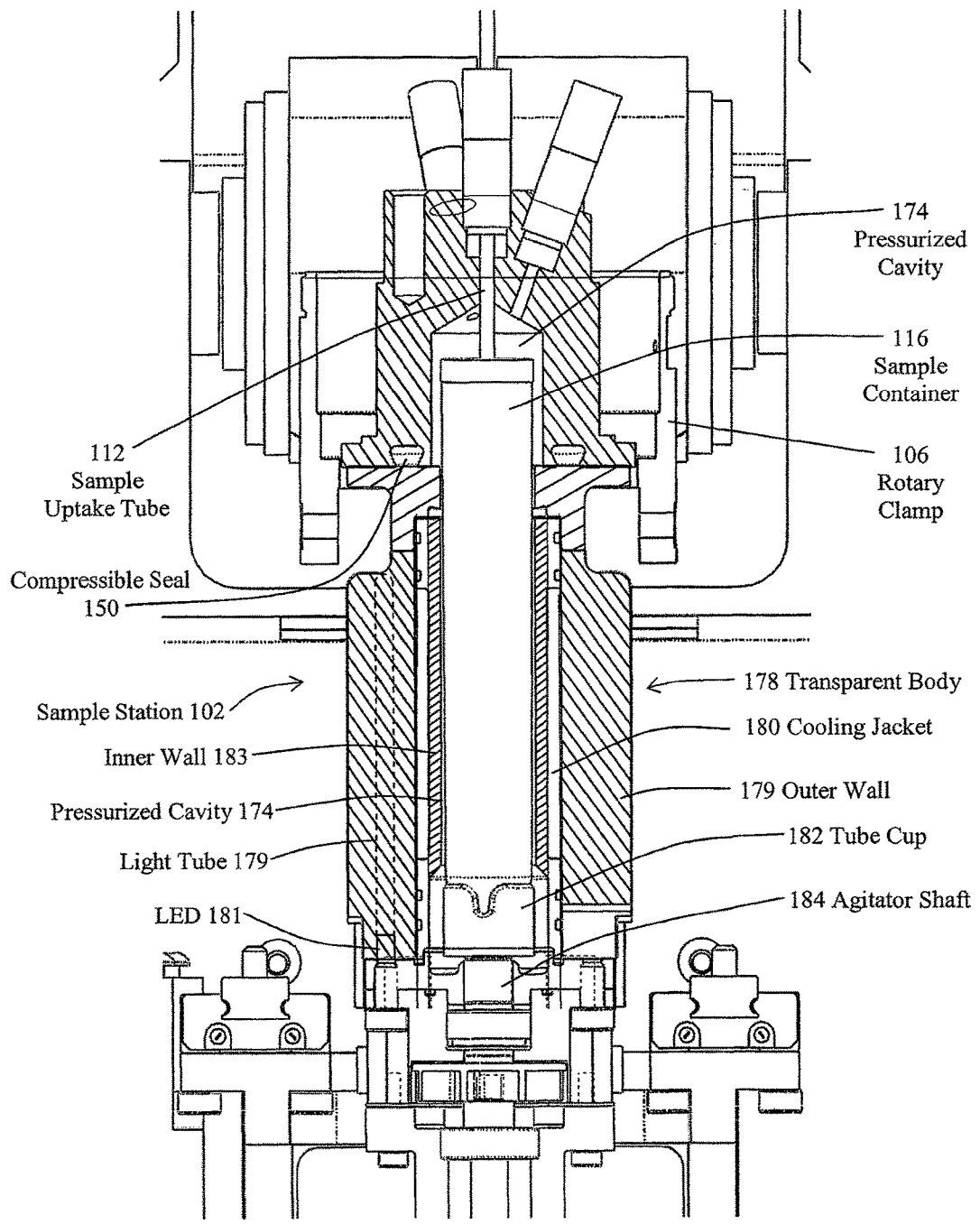
FIG. 8 is a cross-sectional view of an embodiment of a sample station and clamp.

FIG. 8 is a sectional view of an embodiment of a sample station 102 and rotary clamp 106. As illustrated in FIG. 8, the sample uptake tube 112 is inserted in the pressurized cavity 174. The compressible seal 150 seals the sample station 102 to the rotary clamp 106. The pressurized cavity 174 has a very low volume, which minimizes the time required to bring the pressurized cavity 174 to the proper pressure for sampling. As shown in FIG. 8, the entire sample container 116 is disposed within the pressurized cavity 174 so that there is no pressure differential between the outer and inner surfaces of the sample container 116.

In some systems, the sample container 116 is used as the pressurized vessel. If a crack forms in the sample container 116, or if there are defects in the construction of the sample container 116, the sample container 116 will burst and spray sample over the device and possibly onto the user. This is a very unsuitable situation. Other systems use a large cylinder that may be held down with as much as 120 psi air pressure. These systems have a large internal air volume. If there is an instantaneous reduction in air pressure that holds the cylinder down, explosive decompression can occur, which sounds like a shotgun being fired. This is very unsettling to users. In addition, since there is a large volume, it takes additional time to raise the air pressure within the cylinder.

The small internal volume of the pressurized cavity 174, illustrated in FIG. 8, reduces the time required to bring the pressurized cavity 174 to the proper pressure. Additionally, the simple clamping mechanism illustrated in FIGS. 4, 5 and 6 does not require an active force to remain in the clamped and sealed position. The rollers and ramps generate the necessary force to establish a seal and the self-energized o-ring maintains a sealed unit and can remain in the clamped and sealed position without any external application of energy. In fact, the motor 147 (FIG. 5) can be turned off when the rotary clamp 106 is in the clamp position. The transparent body 178 of the sample station 102 allows a user to view the sample container 116 during sampling. The transparent body 178 is constructed from polysulfone. Polysulfone has many desirable properties and is substantially transparent. A light tube 179 is included in the transparent body to illuminate the sample container 116. In addition, the sample container 116 is transparent so that the sample can also be viewed during the sampling process. The light tube 179 transmits light from a LED 181 disposed at the bottom of the light tube. In this manner, minimal heat is transferred to the transparent body 178. The transparent body 178 also includes a cooling jacket 180, which is also transparent to allow for visibility even with fully jacketed cooling. Cooled water flows to the cooling jacket 180 to cool the pressurized cavity 174 and the sample. Inner wall 183 of the transparent body 178 is substantially thinner than the outer wall 179 of the transparent body 178. As such, heat is extracted from the pressurized cavity 174, rather than extracting outside heat because of the relative thicknesses of the inner wall 183 and the outer wall 179 of the transparent body 178. In practice, the water flowing through the jacket 180 can be cooled or warmed, allowing full temperature control of the sample.

As also illustrated in FIG. 8, the sample uptake tube 112 is inserted into a bottom portion of the sample container 116 to draw sample from the bottom of the sample container 116. Sample container 116 sits in a tube cup 182, which is connected to an agitator shaft 184. The agitator shaft 184 moves in an orbital motion that agitates the sample in the sample container 116. By agitating the sample in the sample container 116, the sample cells do not gather at the bottom of the sample container 116, but are mixed and remain in suspension so that a constant and steady stream of sample particles can be withdrawn by sample uptake tube 112.

Figure 9:
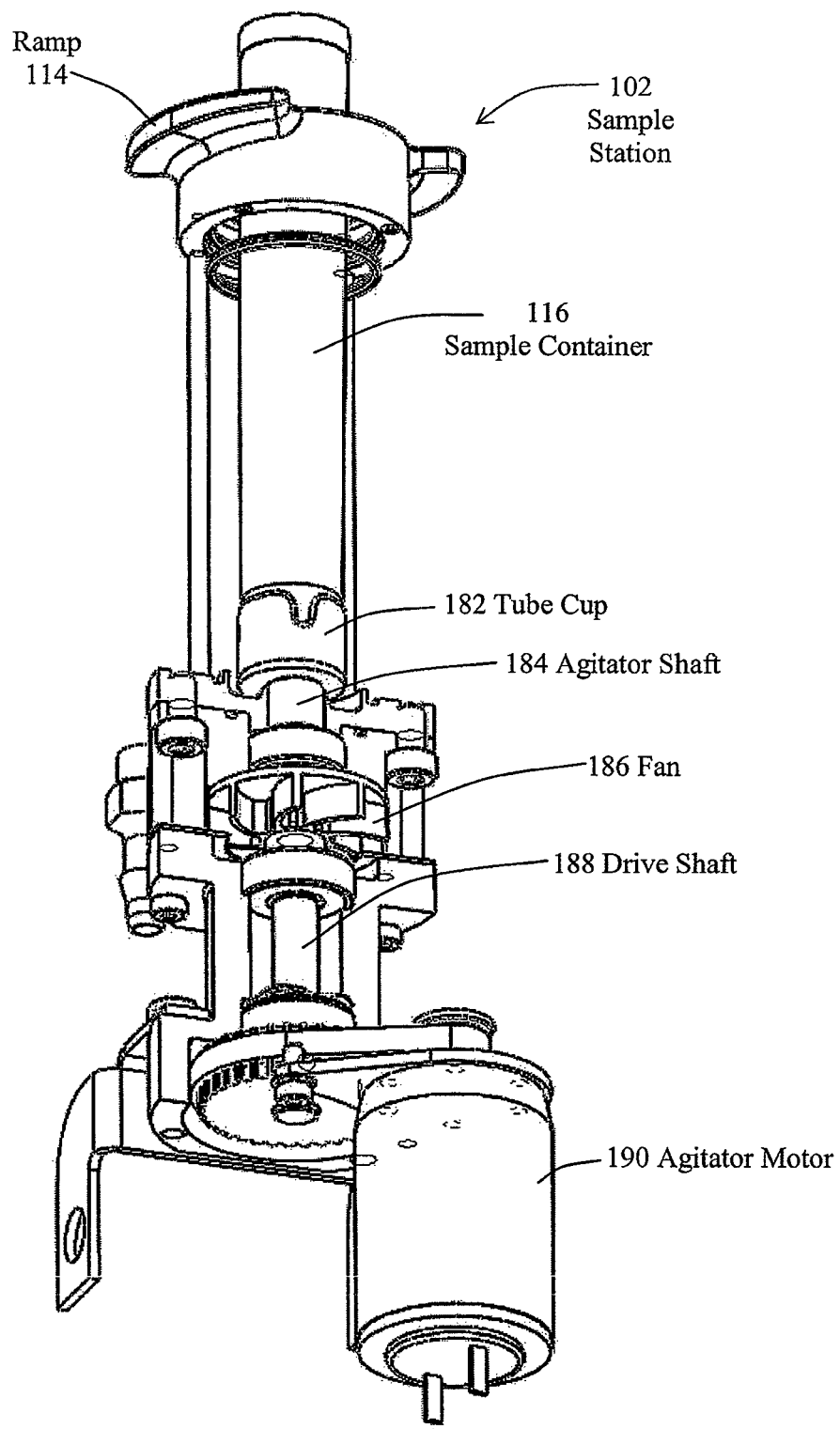
FIG. 9 is an isometric view illustrating portions of the sample station.

FIG. 9 is an isometric view of portions of the sample station 102. As illustrated in FIG. 9, the ramp 114 is connected to the upper portion of the sample station 102. The sample container 116 sits in the tube cup 182, which is driven by an eccentric extension (not shown) on the end of agitator shaft 184. Agitator shaft 184 is driven by a drive shaft 188. The agitator shaft 184 has a small shaft extension (not shown) that is offset from the central axis of the drive shaft 188, which creates an orbital motion of the agitator shaft extension. Fan 186 is connected to the drive shaft 188 and extracts heat from the agitator shaft 184, which can generate heath from friction in its shaft seal when rotating and sealed against pressure in the pressurized cavity 174 (FIG. 8). The removal of heat from the agitator shaft 184 allows the cooling fluid in the cooling jacket 180 (FIG. 8) to more effectively cool the sample in the sample container 116. Agitator motor 190 drives the drive shaft 188 in the manner illustrated in FIG. 9.

Figure 10:
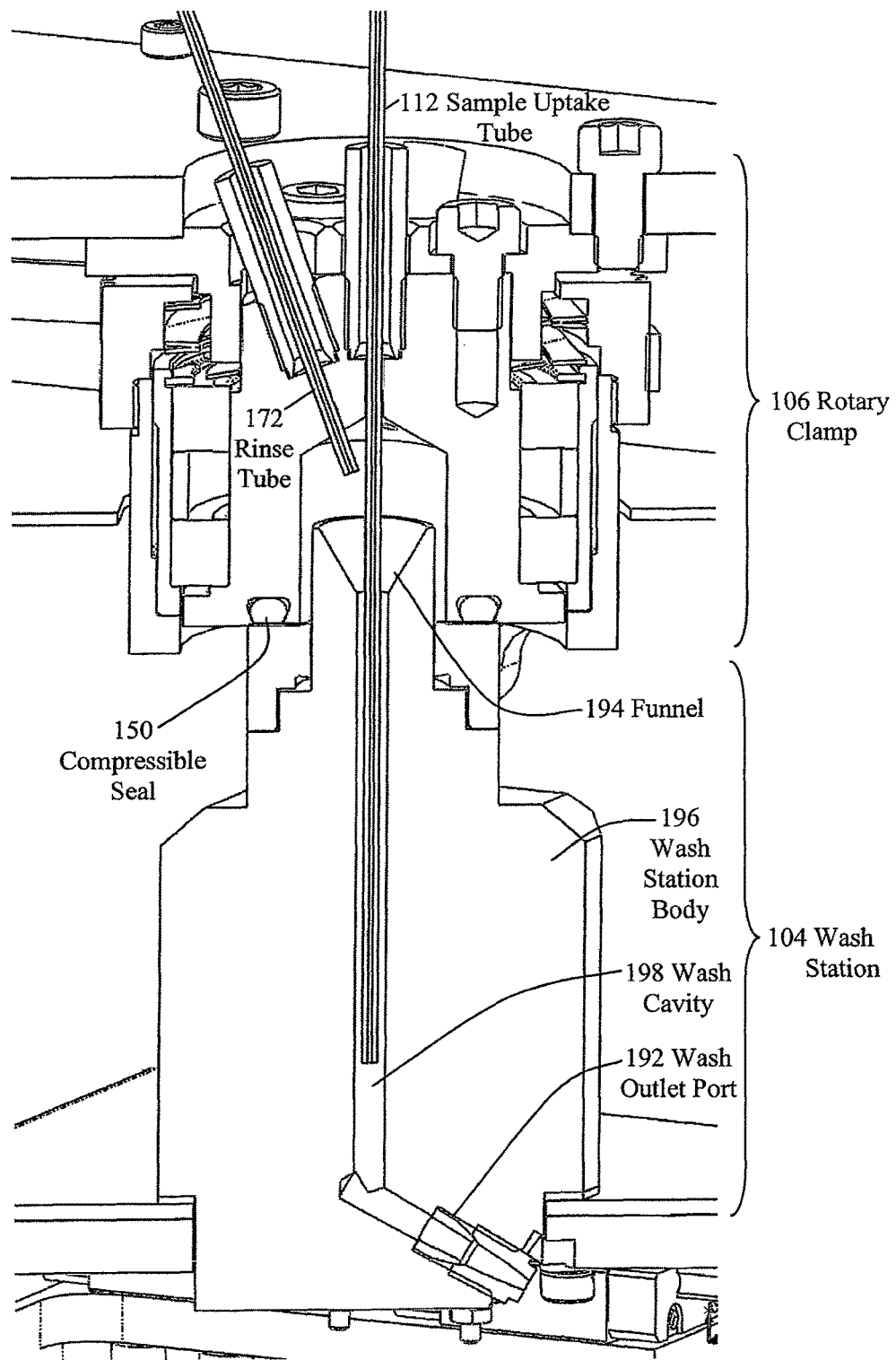
FIG. 10 is a cross-sectional view of an embodiment of a wash station and a clamp.

FIG. 10 is a sectional view of the rotary clamp 106 and wash station 104. As illustrated in FIG. 10, the rotary clamp 106 is positioned over and clamped to the wash station 104. The rotary clamp 106 is sealed to the wash station 104 by the compressible seal 150, which is compressed by forces generated by the ramp 108 and rollers 142, 144 (FIG. 6). During a wash cycle, the sample uptake tube 112 is inserted in the wash cavity 198 of the wash station 104. The wash cavity 198 has dimensions that are slightly greater than the sample uptake tube 112 so that the outer portion of the sample uptake tube 112 can be washed by rinse tube 172. In operation, rinsing fluid 168 flows through the rinse tube 172 into a funnel 194 at an angle so that the rinsing fluid 168 is injected into the wash cavity 198 with a swirling motion. This turbulence and swirling motion of rinsing fluid 168 removes sample cells from the outer portion of the sample uptake tube 112. The wash cavity 198 is formed in the wash station body 196 so that the dimensions of the wash cavity 198 are only slightly greater than the outer dimensions of the sample uptake tube 112. Because only a small cavity is formed between the outer walls of the sample uptake tube 112 and the inner walls of wash cavity 198, the wash fluid contacts the outer surface of the sample uptake tube 112 along a length of the wash cavity 198. A wash outlet port 192 is connected to the bottom portion of the wash cavity 198, which flushes the rinsing fluid 168 from the wash cavity 198. Either deionized water or sheath fluid can be used as rinse fluid 168. Deionized water effectively removes sample cells in a fashion that is somewhat better than using standard sheath fluid.

Hence, the various embodiments show a dual station system, which gives a user access to a sample station during a wash process, increasing the efficiency and work flow process of the overall system. A unique rotary clamp system is employed that accurately creates the necessary pressure to seal both the sample station 102 and wash station 104 to the sample uptake tube 112. The sample station 102 and wash station 104 are accurately guided to the rotary clamp 106 using a guide track. Rotary clamp 106 automatically senses the sample station 102 and wash station 104 and automatically seals the clamp to the sample station 102 and wash station 104. An efficient backflow process is initiated automatically when the wash station 104 is clamped by the rotary clamp 106. In addition, rinse fluid from a rinse tube is injected into a wash cavity at an angle so that the rinse fluid swirls around the outer surfaces of the sample uptake tube to wash the outer surfaces of the sample uptake tube. The pressurized cavity 174 in the sample station 102 is minimized to allow the system to quickly and easily reach the desired pressure level. In addition, a pressure differential does not exist across the sample container 116, which virtually eliminates the chance of bursting the sample container 116 in the pressurized cavity 174. A unique agitation system is employed to agitate the sample in the sample container 116 by inserting the sample container 116 in a tube cup 182 that moves in an orbital motion. The sample station 102 has a transparent body 178, which allows the user to view the sample during the sampling process and ensure that the process is operating properly, that agitation is occurring and can view the level of the sample in the sample container 116. Also, an extremely low heat light pipe is used to assist in viewing the sample in the sample container 116 during the sampling process.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A flow cytometer system comprising:
   a clamp;
   a sample uptake tube passing through the clamp;
   a nozzle;
   sample tubing;
   an injection needle;
   a backflow system;
   a rinsing system; and
   a tray configured to be movable along at least a horizontal axis between a sampling position and a washing position, the tray having a wash station and a sample station that are spaced apart from one another along the horizontal axis and that move in unison with the tray during movement of the tray, wherein the tray is configured such that the sample station is positioned beneath the clamp and the wash station is not positioned beneath the clamp when the tray is in the sampling position and the wash station is positioned beneath the clamp and the sample station is not positioned beneath the clamp when the tray is in the washing position, wherein:
      a first end of the injection needle is in fluidic communication with the sample uptake tube via the sample tubing,
      the injection needle has a second end that is located within the nozzle,
      the wash station is configured to wash parts of a flow cytometer of the flow cytometer system that contact sample particles during a wash cycle,
      the wash station is positioned beneath the clamp during the wash cycle and an end of the sample uptake tube is positioned within the wash station during the wash cycle, the sample station is configured to receive a sample container and to provide access to samples in the sample container by the flow cytometer during a sample cycle, the sample station is positioned beneath the clamp during the sample cycle and the end of the sample uptake tube is positioned within the sample station during the sample cycle, the sample station is accessible to a user during the wash cycle so that the user can place the sample container in the sample station during the wash cycle, the clamp is configured to secure the wash station during the wash cycle and the sample station during the sample cycle, the backflow system is configured to cause first rinsing fluid to flow into the nozzle at a first pressure, through the injection needle and sample tubing and to the wash station via the sample uptake tube at a second pressure lower than the first pressure, thereby rinsing interior surfaces of the nozzle, injection needle, sample tubing, and sample uptake tube to remove the sample particles from the interior surfaces, and the rinsing system is configured to cause second rinsing fluid to be flushed around an outer surface of the sample uptake tube when the sample uptake tube is in the wash station to remove the sample particles from the outer surface.

2. The flow cytometer system of claim 1, wherein the tray is further configured to also be movable along a vertical axis, the system further comprising:

a track that is configured to guide movement of the tray such that vertical movement of the tray between an elevated position and a lowered position occurs without permitting accompanying horizontal movement of the tray for at least a first vertical distance when the sample station is beneath the clamp and also when the wash station is beneath the clamp, wherein the clamp is:
 engageable with the wash station when the tray is in the elevated position and the washing position, and
 engageable with the sample station when the tray is in the elevated position and the sampling position.

3. The flow cytometer system of claim 1, wherein:
the wash station includes a wash station ramp that is connected to the wash station and that has a downward-facing sloped surface following a first helical path having a first center axis that is vertical,
the sample station includes a sample station ramp that is connected to the sample station and that has a downward-facing sloped surface following a second helical path having a second center axis that is parallel to the first center axis, and
the clamp is a rotary clamp that is configured to rotate and to engage with the wash station ramp to secure the wash station to the rotary clamp and form a seal when the wash station is positioned directly beneath the rotary clamp and to rotate and to engage with the sample station ramp to secure the sample station to the rotary clamp and form a seal when the sample station is directly beneath the rotary clamp.

4. The flow cytometer system of claim 1, further comprising a rinse tube that is configured to direct the second rinsing fluid onto the outer surface of the sample uptake tube when the sample uptake tube is in the wash station.

5. The flow cytometer system of claim 4, wherein the wash station includes a wash cavity that is cylindrical, has a diameter slightly larger than the sample uptake tube, and transitions to a funnel, wherein the funnel is configured to cause the second rinsing fluid, when the second rinsing fluid is directed from the rinse tube onto the outer surface of the sample uptake tube, to swirl around the outer surface of the sample uptake tube to remove the sample particles from the outer surface of the sample uptake tube.

6. The flow cytometer system of claim 5, wherein the first and second rinsing fluids comprise deionized water.

7. The flow cytometer system of claim 1, wherein the sample station and the clamp, when the clamp is engaged with the sample station, are configured to enclose the sample container in a low-volume cavity that can be rapidly pressurized to an operating pressure for the sample cycle and not create a pressure differential on the sample container that causes the sample container to burst.

8. The flow cytometer system of claim 7, further comprising an agitation system that is configured to move the sample container in an orbital motion relative to the tray to agitate sample fluid in the sample container when the sample container is inserted into the sample station and the agitation system is activated.

9. A method comprising:
providing the flow cytometer system of claim 1;
 providing the sample container and inserting it into the sample station;
 moving the tray into the sampling position;
 using the sample uptake tube to obtain a sample from the sample station when the tray is in the sampling position;
 moving the tray into the washing position;
 providing the first rinsing fluid and the second rinsing fluid; and
 washing one or more parts of the flow cytometer system, including at least a portion of the sample uptake tube, during the wash cycle by causing, when the tray is in the washing position, the first rinsing fluid to flow backwards through the one or more parts of the flow cytometer, including the sample uptake tube, and by directing the second rinsing fluid around the sample uptake tube in the wash station.

10. The method of claim 9, wherein washing the one or more parts of the flow cytometer system during the wash cycle further comprises causing the first rinsing fluid to flow through the injection needle to the sample tubing and then to the sample uptake tube.

11. The method of claim 9, further comprising:
enclosing the sample container in a low-volume cavity in the sample station; and
rapidly pressurizing the low-volume cavity to an operating pressure while not creating a pressure differential on the sample container that causes the sample container to burst.

12. The method of claim 11, further comprising:
moving a bottom portion of the sample container in an orbital motion to agitate sample fluid in the sample container.

* * * * *